(12) United States Patent  (10) Patent No.: US 9,763,689 B2
Parham  (45) Date of Patent: Sep. 19, 2017

(54) ELONGATED NEEDLES FOR ULTRASONIC APPLICATIONS

(71) Applicant: Tenex Health, Inc., Lake Forest, CA (US)

(72) Inventor: Tate Ray Parham, Silverado, CA (US)

(73) Assignee: Tenex Health, Inc., Lake Forest, CA (US)

( * ) Notice: Subject to any disclaimer, the term of this patent is extended or adjusted under 35 U.S.C. 154(b) by 303 days.

(21) Appl. No.: 14/710,478

(22) Filed: May 12, 2015

(65) Prior Publication Data

US 2016/0331397 A1   Nov. 17, 2016

(51) Int. Cl.
 *A61B 17/32* (2006.01)
 *A61N 7/00* (2006.01)
 *A61B 17/00* (2006.01)

(52) U.S. Cl.
 CPC ........ *A61B 17/320068* (2013.01); *A61N 7/00* (2013.01); *A61B 2017/00526* (2013.01); *A61B 2017/00955* (2013.01)

(58) Field of Classification Search
 CPC .... A61B 17/320068; A61B 17/320092; A61B 2217/007; A61B 2017/320072; A61B 17/32; A61B 2017/320084; A61B 17/22012; A61F 9/00745; A61F 9/00736
 See application file for complete search history.

(56) References Cited

U.S. PATENT DOCUMENTS

| | | | |
|---|---|---|---|
| 3,575,622 A | 4/1971 | Nielson | |
| 3,589,363 A | 6/1971 | Banko | |
| 3,615,366 A * | 10/1971 | Allen | C22C 38/58 148/325 |
| 3,645,725 A * | 2/1972 | Denhard, Jr. | C22C 38/58 420/44 |
| 3,668,758 A * | 6/1972 | Krock | B23K 20/22 228/193 |
| 3,990,452 A | 11/1976 | Murry et al. | |
| 4,188,952 A | 2/1980 | Loschilov et al. | |
| 4,428,748 A | 1/1984 | Peyman | |
| 4,515,583 A | 5/1985 | Sorich | |
| 4,531,934 A | 7/1985 | Kossovsky et al. | |
| 4,750,902 A * | 6/1988 | Wuchinich | A61B 17/22012 604/22 |
| 4,827,911 A * | 5/1989 | Broadwin | A61B 17/22012 310/17 |
| 4,867,141 A | 9/1989 | Nakada et al. | |
| 4,870,953 A | 10/1989 | DonMicheal et al. | |
| 4,920,954 A | 5/1990 | Alliger | |

(Continued)

FOREIGN PATENT DOCUMENTS

| | | |
|---|---|---|
| CN | 2402273 Y | 10/2000 |
| CN | 2774407 Y | 4/2006 |

(Continued)

OTHER PUBLICATIONS

International Application No. PCT/US2016/032055 filed on May 12, 2016.

(Continued)

*Primary Examiner* — Jonathan Miles
(74) *Attorney, Agent, or Firm* — K&L Gates LLP; Louis C. Cullman; Robert W. Winn

(57) ABSTRACT

This disclosure relates to elongated needle assemblies and methods of their manufacture and use.

19 Claims, 2 Drawing Sheets

(56) References Cited

U.S. PATENT DOCUMENTS

| | | | |
|---|---|---|---|
| 4,979,952 A * | 12/1990 | Kubota | A61B 17/22012 310/316.01 |
| 5,038,756 A | 8/1991 | Kepley | |
| 5,042,461 A | 8/1991 | Inoue | |
| 5,108,411 A * | 4/1992 | McKenzie | A61B 8/12 604/264 |
| 5,139,509 A * | 8/1992 | Fischer | A61F 9/00745 604/22 |
| 5,176,677 A * | 1/1993 | Wuchinich | A61F 2/46 604/22 |
| 5,267,954 A | 12/1993 | Nita | |
| 5,275,607 A | 1/1994 | Lo | |
| 5,344,395 A | 9/1994 | Whalen et al. | |
| 5,403,276 A * | 4/1995 | Schechter | A61B 17/32002 604/118 |
| 5,413,556 A | 5/1995 | Whittingham | |
| 5,417,654 A | 5/1995 | Kelman | |
| 5,480,379 A | 1/1996 | La Rosa | |
| 5,514,086 A | 5/1996 | Parisi et al. | |
| 5,520,633 A * | 5/1996 | Costin | A61M 1/0031 601/2 |
| 5,562,609 A | 10/1996 | Brumbach | |
| 5,580,347 A | 12/1996 | Reimels | |
| 5,626,563 A | 5/1997 | Dodge et al. | |
| 5,683,406 A * | 11/1997 | Altobelli | A61B 10/025 30/317 |
| 5,814,016 A | 9/1998 | Valley et al. | |
| 5,897,524 A | 4/1999 | Wortrich et al. | |
| 5,910,110 A | 6/1999 | Bastable | |
| 5,911,700 A | 6/1999 | Mozsary et al. | |
| D418,916 S | 1/2000 | Bastable | |
| 6,033,375 A | 3/2000 | Brumbach | |
| 6,077,285 A | 6/2000 | Boukhny | |
| 6,090,123 A * | 7/2000 | Culp | A61B 90/98 604/22 |
| 6,102,046 A | 8/2000 | Weinstein et al. | |
| 6,139,518 A | 10/2000 | Mozsary et al. | |
| 6,206,014 B1 | 3/2001 | Cameron, III | |
| 6,214,017 B1 | 4/2001 | Stoddard | |
| 6,234,993 B1 | 5/2001 | Terpilowski | |
| 6,270,471 B1 | 8/2001 | Hechel et al. | |
| 6,379,351 B1 | 4/2002 | Thapliyal et al. | |
| 6,402,769 B1 | 6/2002 | Boukhny | |
| 6,437,266 B1 | 8/2002 | Pannenborg | |
| 6,461,301 B2 | 10/2002 | Smith | |
| 6,524,251 B2 | 2/2003 | Rabiner et al. | |
| 6,551,337 B1 | 4/2003 | Rabiner et al. | |
| 6,562,054 B1 | 5/2003 | Weber et al. | |
| 6,623,444 B2 | 9/2003 | Babaev | |
| 6,660,013 B2 | 12/2003 | Rabiner et al. | |
| 6,695,781 B2 | 2/2004 | Rabiner et al. | |
| 6,695,782 B2 | 2/2004 | Ranucci et al. | |
| 6,964,647 B1 | 11/2005 | Babaev | |
| 6,980,419 B2 | 12/2005 | Smith et al. | |
| 7,077,820 B1 | 7/2006 | Kadziauskas et al. | |
| 7,270,656 B2 * | 9/2007 | Gowda | A61N 5/0601 606/15 |
| 7,507,212 B2 | 3/2009 | Tsuchiya et al. | |
| 7,845,235 B2 | 12/2010 | Sandu | |
| 7,850,707 B2 | 12/2010 | Yaguchi et al. | |
| 8,025,672 B2 | 9/2011 | Novak et al. | |
| 8,052,701 B1 * | 11/2011 | Cox | A61B 17/320725 606/159 |
| 8,070,711 B2 | 12/2011 | Bassinger et al. | |
| 8,075,503 B2 | 12/2011 | Jaeb | |
| 8,303,505 B2 | 11/2012 | Webler et al. | |
| 8,382,782 B2 * | 2/2013 | Robertson | A61B 17/320092 606/169 |
| 9,149,291 B2 * | 10/2015 | Parham | A61B 17/320068 |
| 2002/0007200 A1 * | 1/2002 | Desinger | A61B 17/320068 607/96 |
| 2002/0068930 A1 | 6/2002 | Tasto et al. | |
| 2002/0107538 A1 | 8/2002 | Shibata et al. | |
| 2002/0183720 A1 | 12/2002 | Hill et al. | |
| 2004/0133168 A1 | 7/2004 | Salcudean et al. | |
| 2004/0162546 A1 | 8/2004 | Liang | |
| 2004/0259483 A1 | 12/2004 | Newell | |
| 2004/0267121 A1 | 12/2004 | Sarvazyan et al. | |
| 2005/0101984 A1 | 5/2005 | Chanduszko et al. | |
| 2005/0209560 A1 * | 9/2005 | Boukhny | A61M 1/0058 604/118 |
| 2005/0209621 A1 | 9/2005 | Gordon | |
| 2005/0228288 A1 | 10/2005 | Hurst | |
| 2006/0195106 A1 | 8/2006 | Jones et al. | |
| 2006/0241450 A1 | 10/2006 | Da Silva et al. | |
| 2007/0250041 A1 | 10/2007 | Werp | |
| 2007/0255196 A1 | 11/2007 | Wuchinich | |
| 2007/0276352 A1 | 11/2007 | Crocker et al. | |
| 2008/0004621 A1 | 1/2008 | Dahla et al. | |
| 2008/0033349 A1 | 2/2008 | Suzuki | |
| 2008/0033410 A1 | 2/2008 | Rastegar et al. | |
| 2008/0058775 A1 | 3/2008 | Darian et al. | |
| 2008/0195002 A1 | 8/2008 | Thompson et al. | |
| 2008/0234710 A1 | 9/2008 | Neurohr et al. | |
| 2009/0024076 A1 | 1/2009 | Babaev | |
| 2009/0069712 A1 * | 3/2009 | Mulvihill | A61B 10/025 600/564 |
| 2009/0112098 A1 | 4/2009 | Vaezy | |
| 2009/0312693 A1 | 12/2009 | Thapliyal et al. | |
| 2010/0056986 A1 | 3/2010 | Allen | |
| 2010/0076476 A1 | 3/2010 | To | |
| 2010/0211083 A1 | 8/2010 | Sauer | |
| 2010/0312102 A1 | 12/2010 | Barnes | |
| 2011/0015660 A1 * | 1/2011 | Wiener | A61B 17/320092 606/169 |
| 2011/0040212 A1 | 2/2011 | Dietz | |
| 2011/0066174 A1 * | 3/2011 | Gilbert | A61B 17/320092 606/169 |
| 2011/0160620 A1 | 6/2011 | Gill et al. | |
| 2011/0251461 A1 | 10/2011 | Gonzalez et al. | |
| 2012/0078164 A1 | 3/2012 | Mulvihill | |
| 2012/0083728 A1 | 4/2012 | Sorensen | |
| 2012/0209303 A1 * | 8/2012 | Frankhouser | A61B 10/025 606/169 |
| 2013/0331872 A1 | 12/2013 | Parham | |
| 2015/0039005 A1 | 2/2015 | Gill | |
| 2015/0351790 A1 | 12/2015 | Gill et al. | |
| 2016/0059043 A1 | 3/2016 | Gill et al. | |
| 2016/0096040 A1 | 4/2016 | Parham | |

FOREIGN PATENT DOCUMENTS

| | | |
|---|---|---|
| CN | 2879983 Y | 3/2007 |
| CN | 101332340 | 12/2008 |
| EP | 709077 B1 | 10/1996 |
| EP | 1634542 A1 | 3/2006 |
| WO | 2007/143686 A2 | 12/2007 |
| WO | 2008/027223 A2 | 3/2008 |
| WO | 2008/040020 A2 | 4/2008 |
| WO | 2009/105628 | 8/2009 |
| WO | 2012/019136 A2 | 2/2012 |
| WO | 2016/036810 A1 | 3/2016 |
| WO | 2016/054563 A1 | 4/2016 |

OTHER PUBLICATIONS

Labanca et al., Piezoelectric surgery: twenty years of use. British Journal of Oral and Maxillofacial Surgery, 46:265-269 (2008).

Supplementary European Search Report Issued in EP Application No. 10841671, mailed Sep. 5, 2016.

International Search Report and Written Opinion issued in PCT/US2009/034659, mailed Oct. 1, 2009.

International Search Report and Written Opinion issued in PCT/US2010/062341, mailed Mar. 25, 2011.

Kowalewski et al., Issues in Vacuum Brazing, May 1, 2006, available at https://www.secowarwick.com/assets/Documents/Articles/Vacuum-Furnaces/Issues-in-vacuum-brazing-VAC.pdf.

Lin et al., Clinical Outcomes of Ultrasound-Guided Aspiration and Lavage in Calcific Tendinosis of the Shoulder. HSSJ, 3:99-105 (2007), published online 2006.

(56) References Cited

OTHER PUBLICATIONS

Supplementary European Search Report Issued in EP Application No. 09712545, mailed Jun. 20, 2011.
Supplementary European Search Report Issued in EP Application No. 09713554.5, mailed Apr. 15, 2013.
U.S. Appl. No. 14/505,392, filed Oct. 2, 2014.
U.S. Appl. No. 14/475,129, filed Sep. 2, 2014.
International Application No. PCT/US2015/048075 filed on Sep. 2, 2015.
International Application No. PCT/US2015/053812 filed on Oct. 2, 2015.
International Search Report and Written Opinion mailed on Dec. 28, 2015 for International Application No. PCT/US2015/053812 filed on Oct. 2, 2015.
International Search Report and Written Opinion mailed on Nov. 27, 2015 for International Application No. PCT/US2015/048075 filed on Sep. 2, 2015.

* cited by examiner

ELONGATED NEEDLES FOR ULTRASONIC APPLICATIONS

BACKGROUND

The present disclosure is directed to elongated needles assemblies for delivering ultrasonic energy as well as to methods for making and using such assemblies.

DESCRIPTION OF THE RELATED ART

Needles can experience a number of stresses or forces. Of particular concern are those forces that are non-coaxial to the needle, i.e., the direction of the force is not coaxial with the direction of the needle, thereby causing the needles to bend and eventually break. Unfortunately, the force exerts the greatest influence at the point along the needle where the needle is attached to some support structure whether it be a syringe or the horn of an ultrasonic delivery device.

Also, in some settings, such as when delivering ultrasonic energy using a needle, the ultrasonic energy itself can cause the needle to break irrespective of the outside forces applied to the needle.

These problems are exacerbated as the length of the needle increases. Longer needles are desired and/or required for some procedures, and increasing the gauge of the needle is not always an option. Knowing this, practitioners accept that the needle will break more often and need replacing more frequently.

Thus, there exists a need for an elongated needle design that can withstand greater non-coaxial forces, particular when delivering ultrasonic energy and particularly for applications where a long, narrow gauge needle is desired.

SUMMARY

Disclosed herein are needle assemblies for delivering ultrasonic energy. According to some embodiments of the present disclosure, an elongated needle assembly for delivering ultrasonic energy includes a horn, an elongated needle, a sheath or sleeve, and a nose cone. In some embodiments, the horn has a proximal end and a distal end. In some embodiments, the proximal end of the horn is configured to be secured to a hand piece. In some embodiments, the elongated needle extends from the distal end of the horn. In some embodiments, the needle has a proximal end and a distal end, the proximal end being secured to the horn. In some embodiments, the needle comprises a work-hardened material. In some embodiments, the sheath comprises a hollow tube with a proximal end and a distal end. In some embodiments, the sheath substantially encloses at least a portion of the needle. In some embodiments, the nose cone has a proximal end and a distal end, the distal end being secured to the proximal end of the sheath, the proximal end of the nose cone configured to be secured to a hand piece. In some embodiments, the needle is secured to the horn using a brazing process that does not substantially weaken the needle. In some embodiments, the sheath comprises a hardened material, and the sheath is configured to support the needle during the delivery of ultrasonic energy.

According to some embodiments, at least a portion of the proximal end of the needle extends into the horn. In some embodiments, the length of the needle is between about 1.5 inches and about 2.5 inches. In some embodiments, the length of the portion of the needle that extends beyond the horn is between about 1.5 inches and about 2.2 inches. In some embodiments, the length of the needle that extends beyond the horn is between about 1.75 inches and about 2.1 inches. In some embodiments, the length of the needle that extends beyond the horn is at least about 1.9 inches, or at least about 1.99 inches, or about 1.992 inches.

In some embodiments, the needle has a length to diameter ratio of between about 20:1 and about 100:1, between about 30:1 and about 60:1, or between about 35:1 and about 50:1. In some embodiments, the needle has a length to diameter ratio of about 40:1 or about 39.84:1. In some embodiments, the needle has a length to diameter ratio of between about 30:1 and about 60:1, and wherein the sheath has a length to diameter ratio of between about 15:1 and about 25:1. In some embodiments, the needle has a length to diameter ratio of about 40:1 and the sheath has a length to diameter ratio of about 20:1.

In some embodiments, the sheath comprises a work-hardened stainless steel. In some embodiments, the distal end of the nose cone is formed around the proximal end of the sheath in an over-molding procedure. In some embodiments, the nose cone comprises a thermoplastic material. In some embodiments, an inner surface of the sheath and an outer surface of the needle together form a fluid conduit.

According to some embodiments disclosed herein, a method of using an elongated needle assembly includes delivering ultrasonic energy as a part of one of the following medical procedures: urology, plastic surgery, proctology, and wound debridement. In some embodiments, ultrasonic energy is delivered to mix one or more compounds in a difficult-to-access region of the human body.

According to some embodiments disclosed herein, a method of manufacturing an elongated needle assembly includes securing an elongated needle to a horn to form a needle-horn assembly; securing a sheath to a nose cone to form an integral unit; assembling the needle-horn assembly to an ultrasonic handpiece; and assembling the integral unit to the ultrasonic handpiece. In some embodiments, the needle is secured to the horn using a brazing process that does not substantially weaken the needle. In some embodiments, the sheath is secured to the nose cone using an over-molding process in which a distal end of the nose cone is formed around a proximal end of the sheath to form the integral unit. In some embodiments, the sheath comprises a substantially cylindrical material that encloses at least a portion of the needle that extends from the horn. In some embodiments, the sheath is configured to lend support to the needle while still allowing for fluid flow between an inner surface of the sheath and an outer surface of the needle.

In some embodiments, the needle comprises a work-hardened stainless steel. In some embodiments, the sheath comprises a work-hardened stainless steel. In some embodiments, the nose cone comprises a thermoplastic material.

These and other features are disclosed in greater detail in the accompanying figures and the Detailed Description below.

DETAILED DESCRIPTION

The present disclosure is directed to elongated needle assemblies. Such assemblies may be used in ultrasonic applications or any application where extra needle strength is desirable and where longer needles are needed. Also disclosed herein are methods of manufacturing such needles as well as methods in which the needles may be used. However, the present disclosure is not limited to the precise manufacturing methods and applications disclosed herein. Skilled artisans will recognize that other methods could be employed to achieve similar results or that the disclosed methods could be modified without materially changing the scope of this disclosure.

In ultrasonic applications, there is a need for a needle that can transmit ultrasonic energy while maintaining rigidity and strength. According to some embodiments of needle assemblies disclosed herein, a needle, which is secured to a horn, is coupled with a sheath or sleeve and/or a nose cone that is co-molded with the sheath. The sheath may be formed of a rigid material that is configured to provide support to the needle. In some embodiments, co-molding the nose cone with the sheath provides a unitary structure for additional strength.

Providing a stronger sheath—as compared to prior art sheaths—provides support to the needle and allows for a longer needle than would normally be used for delivering ultrasonic energy. Without being tied to any particular theory, it is believed that the closely fitted sheath prevents the needle from bending beyond what it can withstand while still allowing, if desired, the flow of a fluid between the inner surface of the sheath and the outer surface of the needle.

Figure 1:
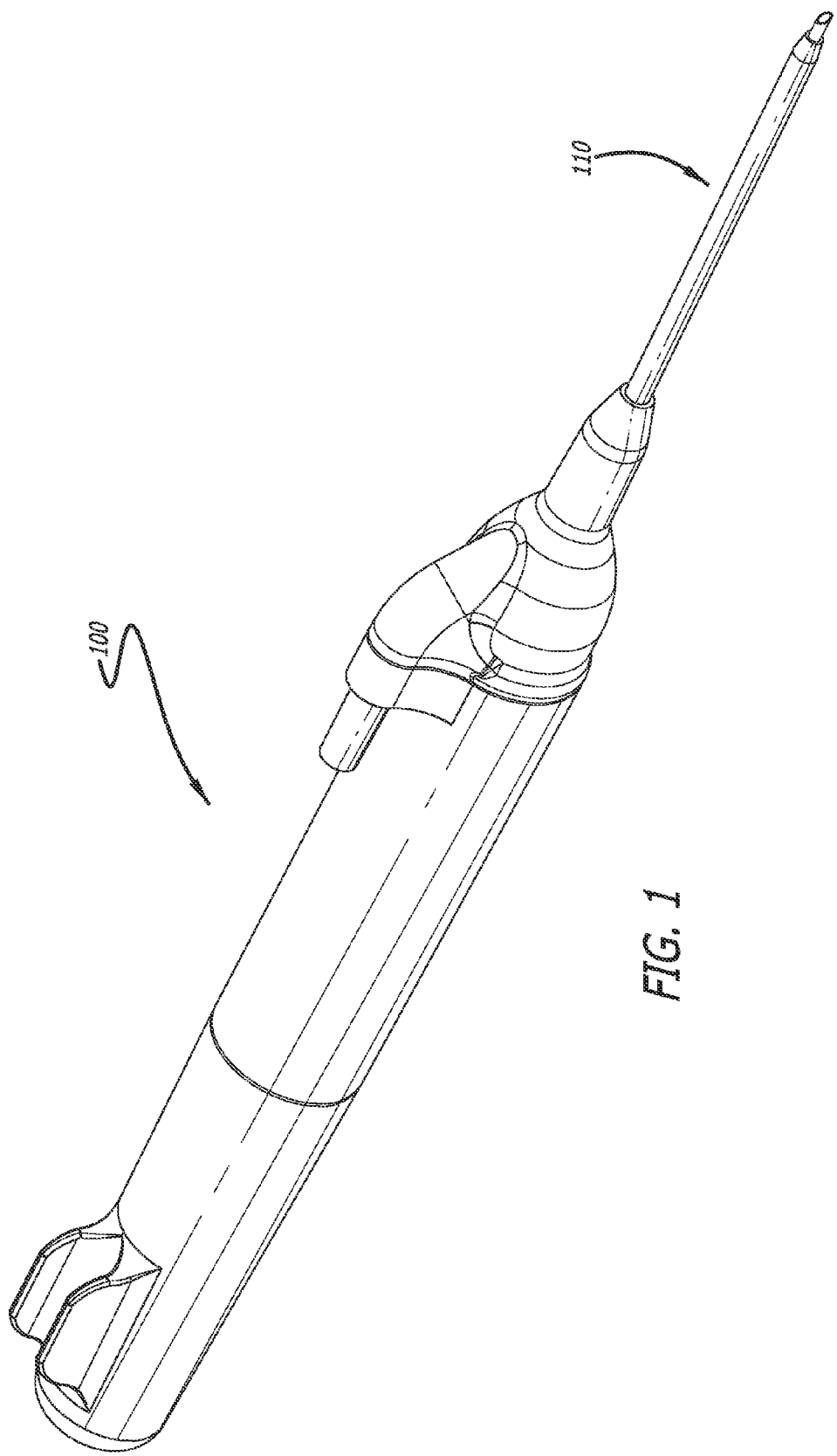
FIG. 1 is a perspective view of an ultrasonic delivery device that includes at its distal end an elongated needle assembly according to some embodiments of the present disclosure.

FIG. 1 illustrates a perspective view of ultrasonic delivery device 100 having a proximal end and a distal end with needle assembly 110 located at the distal end of the device. Needle assembly 110 may be used with any suitable ultrasonic delivery device. Needle assembly 110 may be configured to be secured within the horn of ultrasonic delivery device 100, as disclosed in U.S. Publication Nos. 2010/0312102, 2011/0160620, and 2013/0331872. Each of these disclosures, particularly as they relate to ultrasonic delivery devices, is incorporated herein by reference.

According to some embodiments disclosed herein, a needle assembly comprises a needle secured to a horn and a sheath secured to a nose cone. Both the nose cone and the horn are separately secured to, in some embodiments, a hand piece that generates ultrasonic energy.

Figure 2:
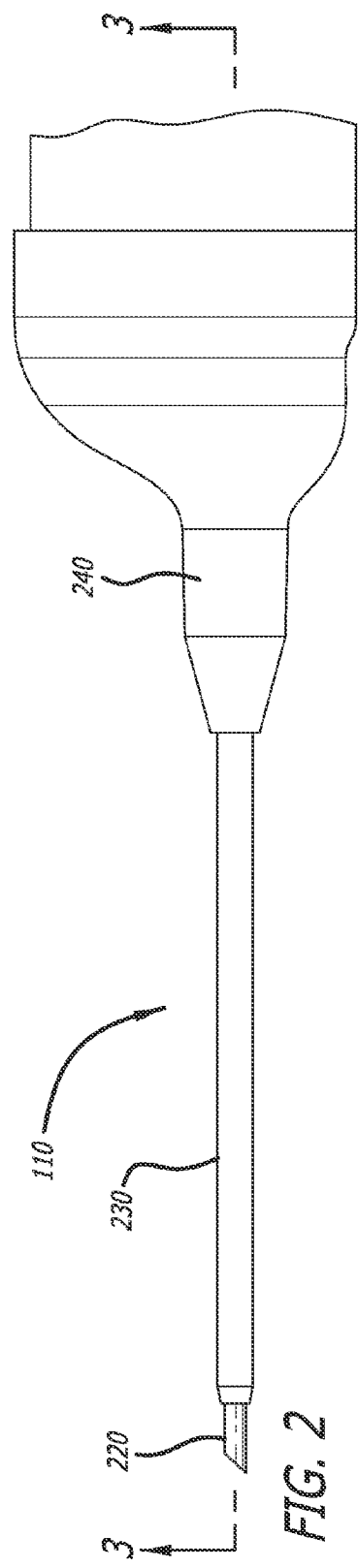
FIG. 2 is a side view of an elongated needle assembly according to some embodiments of the present disclosure.
Figure 3:
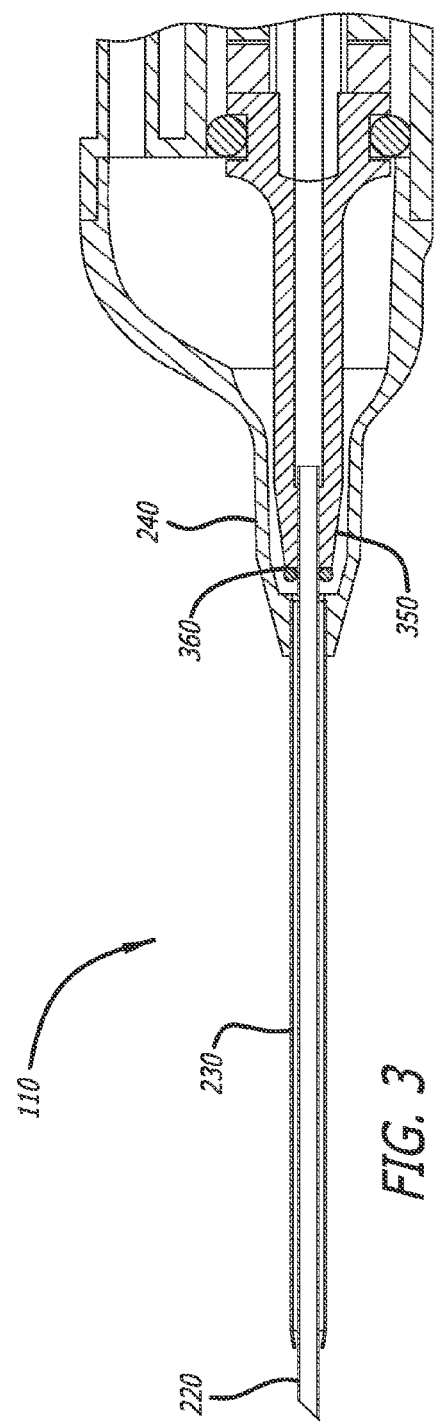
FIG. 3 is a cross-sectional view of the elongated needle assembly of FIG. 2 taken along line 3-3.

FIG. 2 illustrates an embodiment of needle assembly 110. Needle 220 is positioned within sheath 230 and is attached to a horn 350 that is illustrated in FIG. 3. The distal portion of needle 220 extends beyond the distal end and the opening of sheath 230. The proximal portion of sheath 230 is secured to the distal portion of nose cone 240. The proximal portion of nose cone 240 is in turn secured to device 100.

Needle 220, sheath 230, and nose cone 240 may comprise one or more materials. Suitable materials include metals and non-metals. Suitable metals can include titanium, steel, stainless steel, alloys—such as nitinol, amorphous metal alloys (e.g., Liquidmetal and Vitreloy), etc. Suitable non-metals can include ceramics, thermoplastics, polymers, etc. Examples of ceramics include aluminum oxide, aluminum nitride, and zirconia (zirconium dioxide), though other ceramics could also be used. Suitable thermoplastics include high temperature plastics, such as polycarbonate, polyether ether ketone (PEEK), polyetherimides—such as Ultem plastics manufactured by SABIC), polymide-based plastics—such as Vespel manufactured by DuPont. In some embodiments, one or more of needle 220, sheath 230, and nose cone 240 comprise a mixture of materials: two or metals, two or more non-metals, at least one metal and at least one non-metal. In some embodiments, at least one of needle 220, sheath 230, and nose cone 240 comprises a metal coated with a non-metal or more specifically a plastic material.

According to some embodiments where stainless steel is used, the stainless steel is chosen from the 300 series stainless steels (e.g., 302, 303, 304, 304L, 316, and 317). In some embodiments, the stainless steel is chosen from the 200 series stainless steels. In some embodiments, a 300 series stainless steel comprises at least a portion of at least one the needle, the sheath, the horn, or the nose cone. In some embodiments, a 200 series stainless steel comprises at least a portion of at least one the needle, the sheath, the horn, or the nose cone. In some embodiments, the needle and/or the sheath comprise 304 stainless steel.

According to some embodiments, the material comprising at least a portion of the needle is a work-hardened material. For example, a stainless steel may be used that has been hardened by work hardening (also known as strain hardening or cold working), which can occur during a redraw process. In some cases, it is desirable to avoid the use of an annealing process, which could weaken the material. A work-hardened material may also be used for the sheath, the horn, and/or the nose cone.

In some embodiments, the needle comprises a material distinct from the sheath and/or the nose cone. For example, in some embodiments, needle 220 and sheath 230 comprise stainless steel, while nose cone 240 comprises a polymer material. In some embodiments, needle 220 comprises stainless steel, and sheath 230 and nose cone 240 comprise a metal other than stainless steel. In some embodiments, at least one element comprises titanium. For example, in some embodiments, titanium is used as the material for the needle, and a stainless steel is used as the material for the sheath. Without being tied to any theory, it is believed that the strength of titanium could be better harnessed if a sheath comprising a stainless steel is used to lend rigidity to the longer needle running through the sheath.

Needle 220 has a length of about 1.9 inches defined as the distance from the distal end of horn 350, or tip 360, to the distal end of first needle subunit 220. In some embodiments, the length of needle 220 is defined as the distance from the proximal end to the distal end. In some embodiments, the length of the needle assembly is between about 1 inch (about 25.4 mm) and about 4 inches (about 101.6 mm), between about 1.5 inches (about 38.1 mm) and about 3 inches (about 76.2), between about 1.8 inches (about 45.72 mm) and about 2.3 inches (about 58.42), between about 1.85 inches (about 46.99 mm) and about 1.95 inches (about 49.53 mm), or about 1.89 inches (about 48.006 mm. In some embodiments, the length of the needle assembly is at least about 1.5 inches (about 38.1 mm), at least about 1.7 inches (about 43.18 mm), or at least about 1.9 inches (about 48.26 mm). In some embodiments, the length is about 1.99 inches (about 50.546 mm) or about 1.992 inches (about 50.5968 mm).

Needle 220 has a gauge of about 18. In some embodiments, needle 220 has a gauge of between about 12 and about 24, between about 14 and about 22, or between about 16 and about 20. In some embodiments, the gauge of needle 220 is less than about 16, less than about 18, or less than about 20.

Needle 220 has an inner diameter of about 0.05 inches (about 1.27 mm). In some embodiments, needle 220 subunit has an inner diameter of between about 0.01 inches (about 0.254 mm) and about 0.08 inches (about 2.032 mm), between about 0.02 inches (about 0.508 mm) and about 0.05 inches (about 1.27 mm), between about 0.03 inches (about 0.762 mm) and about 0.04 inches (about 1.016 mm), or about 0.038 inches (about 0.9652 mm). In some embodiments, the inner diameter of needle 220 is at least about 0.02 inches (about 0.508 mm), at least about 0.03 inches (about 0.762 mm), or at least about 0.035 inches (about 0.889 mm).

In some embodiments, needle 220 comprises a thin-walled hypodermic tube. In some embodiments, needle 220 comprises a regular-walled hypodermic tube. In some embodiments, needle 220 comprises a thick-walled hypodermic tube.

According to some embodiments, needle 220 has a length of between about 1.7 inches (about 43.18 mm) and about 2.1 inches (about 53.34 mm) and has a gauge between about 16 and about 20. In some embodiments, needle 220 has a length of between about 1.8 inches (about 45.72 mm) and about 2 inches (about 50.8 mm) and has a gauge between about 17 and about 19.

Needle 220 has a length to diameter ratio of about 40:1 where the length is defined as the distance between tip 360 and the distal end of needle 220, and the diameter is the outer diameter of needle 220. In some embodiments, the length to diameter ratio of needle 220 is from about 20:1 to about 150:1, from about 45:1 to about 100:1, or from about 55:1 to about 80:1. In some embodiments, needle 220 has a length to diameter ratio of at least about 25:1, at least about 50:1, at least about 60:1, or at least about 80:1. In some embodiments, the length to diameter ratio of needle 220 is about 38:1.

As illustrated in FIG. 2, the distal portion of needle 220 extends beyond the distal end of sheath 230. In this embodiment, the distance between the distal end of needle 220 and the distal end of sheath 230 is about 0.16 inches (about 4.064 mm). In some embodiments, the distance is between about 0.05 inches (about 1.27) and about 0.5 inches (about 12.7 mm), between about 0.1 inches (about 2.54 mm) and about 0.3 inches (about 7.62 mm), or between about 0.13 inches (about 3.302 mm) and about 0.19 inches (about 4.826 mm). In some embodiments, the distal end of sheath 230 is flush with the distal end of needle 220.

In some embodiments, the distal end of needle 220 extends beyond the distal end of sheath 230 by 2-3 time the diameter of needle 220.

FIG. 3 illustrates a cross-section of needle assembly 110 shown in FIG. 2 taken along line 3-3. In this embodiment, needle 220 has a length that is greater than the length of sheath 230. The distal portion of needle 220, which extends beyond the distal portion of sheath 230, may include a bevel at its tip. The bevel may be made at any number of angles. The embodiment illustrated in FIG. 2 has a bevel of roughly 45 degrees though suitable bevels of about 15 to about 90 degrees could be used.

Needle 220 and sheath 230 are designed to fit closely around each other though not necessary in touching contact. Although contact between needle 220 and sheath 230 would not be contrary to the present disclosure. One benefit of little or no contact between needle 220 and sheath 230 is the ability to transport a fluid between the two surfaces either in or out of the needle. In some embodiments, the presence of a fluid, such as water or saline, may help to lubricate needle 220 and/or maintain the temperature of needle 220.

In some embodiments, the gap or space between an outer surface of needle 220 and an inner surface of sheath 230 is configured to regulate the rate of fluid that flows through handpiece 100. For example, a smaller space will generally allow less fluid to flow while a larger space will generally allow more fluid to flow.

According to some embodiments, the space between needle 220 and sheath 230 is between about 0.001 inches (about 0.0254 mm) and about 0.05 inches (about 1.27 mm).

In some embodiments, the space is between about 0.005 inches (about 0.127 mm) and about 0.02 inches (about 0.508 mm). In some embodiments, the space is about 0.01 inches (about 0.254 mm).

In some embodiments, the space between needle 220 and sheath 230 varies from the proximal end to the distal end. In some embodiments, the space decreases from the proximal end to the distal end. For example, in some embodiments, the space at the proximal end is between about 0.005 inches (about 0.127 mm) and about 0.015 inches (about 0.381 mm), and the space at the distal end is between about 0.001 inches (about 0.0254 mm) and about 0.01 inches (about 0.254 mm). In some embodiments, the space at the proximal end is between about 0.008 inches (about 0.2032 mm) and about 0.013 inches (about 0.3302 mm), and the space at the distal end is between about 0.003 inches (about 0.0762 mm) and about 0.007 inches (about 0.1778 mm). In some embodiments, the space at the proximal end is about 0.01 inches (about 0.254 mm), and the space at the distal end is about 0.005 inches (about 0.127 mm). In some embodiments, the transition between the proximal and distal ends constitutes a gradual taper, a stepped configuration, or a combination thereof. In some embodiments, the transition is achieved by swaging a distal portion of sheath 230.

In some embodiments, sheath 230 supports needle 220 by contacting needle 220 at one or more locations. In some embodiments, at least a portion of an inside surface of sheath 230 contacts at least a portion of an outside surface of needle 220. In some embodiments, the contact point between needle 220 and sheath 230 is located near the distal end of sheath 230.

In some embodiments, sheath 230 supports needle 220 by including one or more support members (not shown) that bridge the gap between sheath 230 and needle 220. In some embodiments, the one or more support members are configured to allow fluid flow through the gap while still providing support.

In some embodiments, sheath 230 comprises a thin-walled hypodermic tube. In some embodiments, sheath 230 comprises a regular-walled hypodermic tube. In some embodiments, sheath 230 comprises a thick-walled hypodermic tube.

According to some embodiments, sheath 230 has a length, defined as the distance between the distal end of nose cone 240 and the distal end of sheath 230, that is between about 1.2 inches (about 30.48 mm) and about 2 inches (about 50.8 mm). In some embodiments, the length of sheath 230 is between about 1.4 inches (about 35.56 mm) and about 1.7 inches (about 43.18 mm). In some embodiments, the length of sheath 230 is about 1.6 inches (about 40.64 mm).

Sheath 230 has a gauge of about 14. In some embodiments, sheath 230 has a gauge of between about 11 and about 17, between about 12 and about 16, or between about 13 and about 15. In some embodiments, the gauge of sheath 230 is smaller than about 12, less than about 13, or less than about 14.

Sheath 230 has an inner diameter of about 0.063 inches (about 1.6 mm). In some embodiments, sheath 230 has an inner diameter of between about 0.03 inches (about 0.762 mm) and about 0.09 inches (about 2.286), between about 0.04 inches (about 1.016 mm) and about 0.08 inches (about 2.032 mm), or between about 0.05 inches (about 1.27 mm) and about 0.07 inches (about 1.778 mm). In some embodiments, the inner diameter of sheath 230 is at least about 0.04 inches (about 1.016 mm), at least about 0.05 inches (about 1.27 mm), or at least about 0.06 inches (about 1.524 mm).

Sheath 230 has a length to diameter ratio of about 19:1 or 20:1 where the length is defined as the distance between the tip of nose cone 240 and the distal end of sheath 230, and the diameter is the outer diameter. In some embodiments, the length to diameter ratio of sheath 230 is from about 10:1 to about 50:1, from about 15:1 to about 30:1, or from about 17:1 to about 25:1. In some embodiments, sheath 230 has a length to diameter ratio of at least about 15:1, at least about 19:1, or at least about 20:1.

Without being limited to any particular theory, it is believed that lengthening needle 220 requires shortening horn 350. In other words, the present inventor has found that an increase in the mass of needle 220 may require a decrease in the mass of horn 350 if a particular ultrasonic frequency is to be maintained.

According to some embodiments, a desirable ultrasonic frequency range includes frequencies between about 20 kHz and about 40 kHz. In some embodiments, a narrower range is desirable, such as between about 20-25 kHz, between about 25-30 kHz, between about 30-35 kHz, between about 35-40 kHz, between about 20-30 kHz, between about 30-40 kHz, and between about 25-35 kHz, though other broader or narrower frequencies ranges may be desirable and are contemplated based on the tissue or material to which the ultrasonic energy is to be delivered and in what context.

FIG. 3 illustrates that needle 220 is secured to horn 350 using any suitable process, which can include brazing, welding, crimping, friction fit, etc. In the illustrated embodiment, needle 220 is secured to horn 350 using a brazing process at tip 360. Tip 360 comprises a recessed portion configured to receive a brazing material. The brazing material contacts horn 350 and needle 220.

In some embodiments, the needle assembly is additionally or alternatively secured to the horn at a point inside the horn within or inside of tip 360.

When any non-coaxial force is applied to a needle attached to a horn, such as occurs in ultrasonic applications, the needle experiences the greatest effect of that force at the location of attachment with the horn. If the non-coaxial force is strong enough or after enough exposure to the non-coaxial force, the needle may fracture and break at the attachment location.

With the extended needle supported within the sheath, a parallel beam structure results that provides a surprising amount of strength to the overall needle assembly particularly when the sheath comprises a rigid material or strengthened material and is designed to closely conform to the shape of the needle. Without being tied to any particular theory, it is believed that the use of a strengthened sheath distributes the effects of a non-coaxial force along the length of the needle rather than focusing those effects only at the location where the needle is attached to the horn.

According to some embodiments, a brazing process is used that does not anneal the materials of the needle and/or the horn. For example, in some embodiments, needle 220 comprises a work-hardened stainless steel that weakens when annealed. However, using a brazing process according to the present disclosure that does not heat the needle to its annealing temperature leaves the needles strength unaffected while still brazing the needle to the horn.

Suitable brazing materials that may be used according to the present disclosure include aluminum-silicon, copper, copper-silver, copper-zinc, gold-nickel, nickel alloy, silver, amorphous brazing foil using nickel, iron, copper, silicon, boron, phosphorus, or similar material, or a combination thereof.

In some embodiments, a brazing process is performed at a temperature below about 1,200° C., below about 1,000° C., below about 700° C., below about 500° C., below about 350° C., or below about 300° C. In some embodiments, a brazing process is performed for no more than about 60 seconds, no more than about 30 seconds, no more than about 10 seconds, no more than about 8 seconds, or no more than about 5 seconds. According to some embodiments, a brazing process is performed at a temperature of between about 500° C. and about 700° C. and for a duration of between about 2 seconds and about 8 seconds.

In some embodiments, the purpose of the brazing process is to cause a preformed brazing material to flow into the junction between horn 350 and needle 220 located at tip 360. To achieve this, the material is heated by heating horn 350 to an adequate temperature and maintaining that temperature for as long as it takes for the brazing material to flow into the junction. In some cases, the temperature is between about 580° C. and about 600° C., and the duration is about 3 to about 7 seconds.

In some instances, too much heat can cause at least part of the needle to anneal, thereby reducing its strength. Thus, the brazing process is carefully controlled (for example, by limiting the temperature and/or the duration) so as to limit the amount of heat energy transferred to the needle from either the horn or the brazing material.

In some embodiments, using a brazing process according to the present disclosure achieves a unitary, continuous, and/or homogenous structure. Without being tied to any particular theory, it is believed that a homogenous structure acts as a better conduit for ultrasonic energy transferred from an ultrasonic delivery device to a target site or a target tissue. In some embodiments, the brazing of the needle to the horn achieves a unitary assembly.

According to some embodiments, sheath 230 is secured to nose cone 240 using a process that creates a strong connection between the two elements. In some embodiments, the connection results in an effectively unitary element. In some embodiments, an over-molding process is used in which a proximal portion or end of sheath 230 is inserted into a distal portion of a mold. The material that will form nose cone 240 is then injected into the mold and formed around the proximal end of sheath 230. In some embodiments, sheath 230 is formed of a thermoplastic material. In some embodiments, sheath 230 is formed of a metal. In some embodiments, sheath 230 comprises more than one material, with one or more of the materials including a thermoplastic material and a metal.

In some embodiments, the amount of the proximal portion of sheath 230 that is enclosed by nose cone 240 may vary. In the embodiment shown in FIG. 3, the amount is about 0.1 inches (about 2.54 mm). In some embodiments, that amount is between about 0.05 inches (about 1.27 mm) and about 0.3 inches (about 7.62 mm), between about 0.1 inches (about 2.54 mm) and about 0.2 inches (about 5.08 mm), or between about 0.1 inches (about 2.54 mm) and about 0.15 inches (about 3.81 mm).

According to some embodiments, sheath 230 is welded to nose cone 240. In some embodiments, nose cone 240 comprises a metal, and the connection between the respective surfaces of sheath 230 and of nose cone 240 comprises a welded joint.

As illustrated in FIG. 3, there is a small gap between the proximal end of sheath 230 and the distal end of horn 350. In some embodiments, this gap is maintained so as to limit the transfer of ultrasonic energy from the horn to the sheath. The size of this gap may depend on the dimensions of the various elements (i.e., the horn, the needle, the nose cone, and the sheath) and/or the frequency at which the ultrasonic energy is delivered. The size of this gap may also depend on the amount, rate, or type of fluid that may be flowing through the needle assembly.

The needle assemblies disclosed herein may be used for any suitable purpose where strength is desired but a relatively long but narrow needle is required. For example, the needle assemblies are suitable for the delivery of ultrasonic energy, particular where the target of the energy requires a longer needle and/or the target is relatively hard so as to pose a greater structural threat to the needle. In the medical context, such targets can include musculoskeletal tissues such as bone.

According to some embodiments, the needle assemblies disclosed herein can be used in cannula applications, such as in urology, plastic surgery, and proctology.

According to some embodiments, the needle assemblies disclosed herein are used for ultrasonic mixing. In some instances an ultrasonic needle used for mixing compounds is needed to access a hard to reach area. The present needle designs allow for transmission of ultrasonic power to a difficult-to-reach area to mix a material located in that area.

EMBODIMENTS

Embodiment 1

An elongated needle assembly for delivering ultrasonic energy, the needle assembly comprising: a horn having a proximal end and a distal end, the proximal end configured to be secured to a hand piece; an elongated needle extending from the distal end of the horn, the needle having a proximal end and a distal end, the proximal end being secured to the horn, the needle comprising a work-hardened material; a sheath comprising a hollow tube with a proximal end and a distal end, the sheath substantially enclosing at least a portion of the needle; a nose cone having a proximal end and a distal end, the distal end being secured to the proximal end of the sheath, the proximal end of the nose cone configured to be secured to the hand piece; wherein the needle is secured to the horn using a brazing process that does not substantially weaken the needle; and wherein the sheath is configured to support the needle during the delivery of ultrasonic energy.

Embodiment 2

The elongated needle assembly of embodiment 1:, wherein at least a portion of the proximal end of the needle extends into the horn.

Embodiment 3

The elongated needle assembly of embodiment 1 or 2, wherein the length of the needle is between about 1.5 inches and about 2.5 inches.

Embodiment 4

The elongated needle assembly embodiment 1, 2, or 3, wherein the length of the portion of the needle that extends beyond the horn is between about 1.5 inches and about 2.2 inches.

Embodiment 5

The elongated needle assembly of embodiment 1, 2, 3, or 4, wherein the length of the needle that extends beyond the horn is between about 1.75 inches and about 2.1 inches.

Embodiment 6

The elongated needle assembly of embodiment 1, 2, 3, 4, or 5 wherein the length of the needle that extends beyond the horn is at least about 1.9 inches.

Embodiment 7

The elongated needle assembly of embodiment 1, 2, 3, 4, 5, or 6, wherein the needle has a length to diameter ratio of between about 35:1 and about 50:1.

Embodiment 8

The elongated needle assembly of embodiment 1, 2, 3, 4, 5, 6, or 7, wherein the needle has a length to diameter ratio of about 40:1.

Embodiment 9

The elongated needle assembly of embodiment 1, 2, 3, 4, 5, 6, or 7, wherein the needle has a length to diameter ratio of between about 35:1 and about 45:1, and wherein the sheath has a length to diameter ratio of between about 15:1 and about 25:1.

Embodiment 10

The elongated needle assembly of embodiment 1, 2, 3, 4, 5, 6, or 7, wherein the needle has a length to diameter ratio of about 40:1 and the sheath has a length to diameter ratio of about 20:1.

Embodiment 11

The elongated needle assembly of embodiment 1, 2, 3, 4, 5, 6, 7, 8, 9, or 10, wherein the sheath comprises a work-hardened stainless steel.

Embodiment 12

The elongated needle assembly of embodiment 1, 2, 3, 4, 5, 6, 7, 8, 9, 10, or 11, wherein the distal end of the nose cone is formed around the proximal end of the sheath in an over-molding procedure.

Embodiment 13

The elongated needle assembly of embodiment 1, 2, 3, 4, 5, 6, 7, 8, 9, 10, 11, or 12, wherein the nose cone comprises a thermoplastic material.

Embodiment 14

The elongated needle assembly of embodiment 1, 2, 3, 4, 5, 6, 7, 8, 9, 10, 11, 12, or 13, wherein an inner surface of the sheath and an outer surface of the needle together form a fluid conduit.

Embodiment 15

A method of using the elongated needle assembly of embodiment 1, 2, 3, 4, 5, 6, 7, 8, 9, 10, 11, 12, 13, or 14 to deliver ultrasonic energy, wherein the ultrasonic energy is delivered as a part of one of the following medical procedures: urology, plastic surgery, proctology, and wound debridement.

Embodiment 16

A method of using the elongated needle assembly of embodiment 1, 2, 3, 4, 5, 6, 7, 8, 9, 10, 11, 12, 13, 14, or 15 to deliver ultrasonic energy to mix one or more compounds in a difficult-to-access region of the human body.

Embodiment 17

A method of manufacturing an elongated needle assembly, the method comprising: securing an elongated needle to a horn using a brazing process that does not substantially weaken the needle, the needle and horn forming a needle-horn assembly; securing a sheath to a nose cone using an over-molding process in which a distal end of the nose cone is formed around a proximal end of the sheath to form an integral unit; assembling the needle-horn assembly to an ultrasonic handpiece; assembling the integral unit to the ultrasonic handpiece, wherein the sheath comprises a substantially cylindrical material that encloses at least a portion of the needle that extends from the horn; and wherein the sheath is configured to lend support to the needle while still allowing for fluid flow between an inner surface of the sheath and an outer surface of the needle.

Embodiment 18

The method of embodiment 17, wherein the needle comprises a work-hardened stainless steel.

Embodiment 19

The method of embodiment 17 or 18, wherein the sheath comprises a work-hardened stainless steel.

Embodiment 20

The method of embodiment 17, 18, or 19, wherein the nose cone comprises a thermoplastic material.

Embodiment 21

An elongated needle assembly for delivering ultrasonic energy, the needle assembly comprising: a horn configured to be secured to a hand piece; an elongated needle secured to the horn, at least a portion extending from the horn; a nose cone secured to the hand piece; a sheath comprising a hollow tube substantially enclosing at least a portion of the needle, the sheath secured to the hand piece; wherein the portion of the needle that extends from the horn is at least about 1.5 inches in length.

Embodiment 22

The needle assembly of embodiment 21, wherein the needle comprises a work-hardened material.

Embodiment 23

The needle assembly of embodiment 21 or 22, wherein the needle comprises a work-hardened stainless steel.

Embodiment 24

The needle assembly of embodiment 21, 22, or 23, wherein the needle is secured to the horn using a process that does not weaken the strength of the needle.

Embodiment 25

The needle assembly of embodiment 21, 22, 23, or 24, wherein the needle is secured to the horn using a brazing process.

Embodiment 26

The needle assembly of embodiment 21, 22, 23, 24, or 25, wherein the portion of the needle that extends from the horn is at least about 1.75 inches in length.

Embodiment 27

The needle assembly of embodiment 21, 22, 23, 24, 25, or 26 wherein the portion of the needle that extends from the horn is at least about 1.9 inches in length.

Embodiment 28

The needle assembly of embodiment 21, 22, 23, 24, 25, 26, or 27, wherein the needle has a length to diameter ratio of between about 35:1 and about 50:1.

Embodiment 29

The needle assembly of embodiment 21, 22, 23, 24, 25, 26, 27, or 28, wherein the needle has a length to diameter ratio of about 40:1.

Embodiment 30

The needle assembly of embodiment 21, 22, 23, 24, 25, 26, 27, 28, or 29, wherein the needle has a length to diameter ratio of between about 35:1 and about 45:1, and wherein the sheath has a length to diameter ratio of between about 15:1 and about 25:1.

Embodiment 31

The needle assembly of embodiment 21, 22, 23, 24, 25, 26, 27, 28, 29, or 30, wherein the needle has a length to diameter ratio of about 40:1 and the sheath has a length to diameter ratio of about 20:1.

Embodiment 32

The needle assembly of embodiment 21, 22, 23, 24, 25, 26, 27, 28, 29, 30, or 31, wherein the sheath comprises a work-hardened stainless steel.

Embodiment 33

The needle assembly of embodiment 21, 22, 23, 24, 25, 26, 27, 28, 29, 30, 31, or 32, wherein a distal end of the nose cone is formed around a proximal end of the sheath in an over-molding procedure.

Embodiment 34

The needle assembly of embodiment 21, 22, 23, 24, 25, 26, 27, 28, 29, 30, 31, 32, or 33, wherein the nose cone comprises a thermoplastic material.

Embodiment 35

The needle assembly of embodiment 21, 22, 23, 24, 25, 26, 27, 28, 29, 30, 31, 32, 33, or 34, wherein an inner surface of the sheath and an outer surface of the needle together form a fluid conduit.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. In one embodiment, the terms "about" and "approximately" refer to numerical parameters within 10% of the indicated range.

The terms "a," "an," "the," and similar referents used in the context of describing the embodiments of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of the present disclosure. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventor for carrying out the embodiments of the present disclosure. Of course, variations on these described embodiments will become apparent to those of ordinary skill in the art upon reading the foregoing description. The inventor expects skilled artisans to employ such variations as appropriate, and the inventor intends for the embodiments of the present disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of this disclosure so claimed are inherently or expressly described and enabled herein.

In closing, it is to be understood that the embodiments disclosed herein are illustrative of the principles of the present disclosure. Other modifications that may be employed are within the scope of this disclosure. Thus, by way of example, but not of limitation, alternative configurations of the embodiments of the present disclosure may be utilized in accordance with the teachings herein. Accordingly, the present disclosure is not limited to that precisely as shown and described.

The invention claimed is:

1. An elongated needle assembly for delivering ultrasonic energy, the needle assembly comprising:
   - a horn having a proximal end and a distal end, the proximal end configured to be secured to a hand piece;
   - an elongated needle extending from the distal end of the horn, the needle having a proximal end and a distal end, the proximal end being secured to the horn, the needle comprising a work-hardened material;
   - a sheath comprising a hollow tube with a proximal end and a distal end, the sheath substantially enclosing at least a portion of the needle;
   - a nose cone having a proximal end and a distal end, the distal end being secured to the proximal end of the sheath, the proximal end of the nose cone configured to be secured to the hand piece;
   - wherein the needle is secured to the horn using a brazing process that does not substantially weaken the needle; and
   - wherein the sheath is configured to support the needle during the delivery of ultrasonic energy.

2. The elongated needle assembly of claim 1, wherein at least a portion of the proximal end of the needle extends into the horn.

3. The elongated needle assembly of claim 1, wherein the length of the needle is between about 1.5 inches and about 2.5 inches.

4. The elongated needle assembly of claim 1, wherein the length of the needle that extends beyond the horn is between about 1.75 inches and about 2.1 inches.

5. The elongated needle assembly of claim 1, wherein the length of the needle that extends beyond the horn is at least about 1.9 inches.

6. The elongated needle assembly of claim 1, wherein the needle has a length to diameter ratio of between about 30:1 and about 60:1.

7. The elongated needle assembly of claim 1, wherein the needle has a length to diameter ratio of about 40:1.

8. The elongated needle assembly of claim 1, wherein the needle has a length to diameter ratio of between about 35:1 and about 45:1, and wherein the sheath has a length to diameter ratio of between about 15:1 and about 25:1.

9. The elongated needle assembly of claim 1, wherein the needle has a length to diameter ratio of about 40:1 and the sheath has a length to diameter ratio of about 20:1.

10. The elongated needle assembly of claim 1, wherein the sheath comprises a work-hardened stainless steel.

11. The elongated needle assembly of claim 1, wherein the distal end of the nose cone is formed around the proximal end of the sheath in an over-molding procedure.

12. The elongated needle assembly of claim 1, wherein the nose cone comprises a thermoplastic material.

13. The elongated needle assembly of claim 1, wherein an inner surface of the sheath and an outer surface of the needle form a fluid conduit.

14. A method of using the elongated needle assembly of claim 1 to deliver ultrasonic energy, wherein the ultrasonic energy is delivered as a part of one of the following medical procedures: urology, plastic surgery, proctology, and wound debridement.

15. A method of using the elongated needle assembly of claim 1 to deliver ultrasonic energy to mix one or more compounds in a difficult-to-access region of the human body.

16. A method of manufacturing an elongated needle assembly, the method comprising:
   securing an elongated needle to a horn using a brazing process that does not substantially weaken the needle, the needle and horn forming a needle-horn assembly;
   securing a sheath to a nose cone using an over-molding process in which a distal end of the nose cone is formed around a proximal end of the sheath to form an integral unit;
   assembling the needle-horn assembly to an ultrasonic handpiece;
   assembling the integral unit to the ultrasonic handpiece, wherein the sheath comprises a substantially cylindrical material that encloses at least a portion of the needle that extends from the horn; and
   wherein the sheath is configured to lend support to the needle while still allowing for fluid flow between an inner surface of the sheath and an outer surface of the needle.

17. The method of claim 16, wherein the needle comprises a work-hardened stainless steel.

18. The method of claim 16, wherein the sheath comprises a work-hardened stainless steel.

19. The method of claim 16, wherein the nose cone comprises a thermoplastic material.

* * * * *